(12) United States Patent
Heesch

(10) Patent No.: US 9,770,569 B2
(45) Date of Patent: Sep. 26, 2017

(54) METHOD FOR MEASURING THE ANESTHETIC AGENT CONSUMPTION IN A VENTILATION SYSTEM

(75) Inventor: Ralf Heesch, Lübeck (DE)

(73) Assignee: DRÄGERWERK AG & CO. KGAA, Lübeck (DE)

(*) Notice: Subject to any disclaimer, the term of this patent is extended or adjusted under 35 U.S.C. 154(b) by 2095 days.

(21) Appl. No.: 11/806,292

(22) Filed: May 31, 2007

(65) Prior Publication Data

US 2008/0029092 A1  Feb. 7, 2008

(30) Foreign Application Priority Data

Jun. 10, 2006 (DE) .................. 10 2006 027 052

(51) Int. Cl.
| | | |
|---|---|---|
| *A61M 16/10* | (2006.01) | |
| *A61M 16/01* | (2006.01) | |
| *A61M 16/18* | (2006.01) | |
| *A61M 16/00* | (2006.01) | |
| *A61M 16/12* | (2006.01) | |
| *A61M 16/22* | (2006.01) | |

(52) U.S. Cl.
CPC .......... *A61M 16/104* (2013.01); *A61M 16/01* (2013.01); *A61M 16/10* (2013.01); *A61M 16/18* (2013.01); *A61M 16/0051* (2013.01); *A61M 16/0063* (2014.02); *A61M 16/0072* (2013.01); *A61M 16/12* (2013.01); *A61M 16/22* (2013.01); *A61M 2016/0039* (2013.01); *A61M 2016/0042* (2013.01); *A61M 2016/102* (2013.01); *A61M 2016/103* (2013.01); *A61M 2016/1025* (2013.01); *A61M 2016/1035* (2013.01)

(58) Field of Classification Search
CPC ...... A61M 16/00; A61M 16/01; A61M 16/10; A61M 16/104; A61M 16/18; A61M 2016/102; A61M 2016/1035
USPC ............ 128/204.18, 203.14, 200.24, 202.22, 128/203.12, 203.15, 203.25, 204.22, 128/205.11
See application file for complete search history.

(56) References Cited

U.S. PATENT DOCUMENTS

| | | | | |
|---|---|---|---|---|
| 4,587,966 A | * | 5/1986 | Albarda | 128/202.22 |
| 4,794,921 A | * | 1/1989 | Lindkvist | 128/203.29 |
| 5,094,235 A | | 3/1992 | Westenskow et al. | |
| 5,520,172 A | | 5/1996 | Obermayer | |
| 5,619,986 A | | 4/1997 | Werner et al. | |
| 5,632,269 A | * | 5/1997 | Zdrojkowski | A61M 16/0051 128/204.21 |
| 5,673,688 A | * | 10/1997 | Tham | A61M 16/104 128/204.22 |
| 5,730,119 A | * | 3/1998 | Lekholm | 128/200.24 |
| 5,771,882 A | | 6/1998 | Psaros et al. | |
| 5,806,513 A | | 9/1998 | Tham et al. | |
| 5,857,458 A | * | 1/1999 | Tham | A61M 16/10 128/203.12 |

(Continued)

*Primary Examiner* — Justine Yu
*Assistant Examiner* — Colin W Stuart
(74) *Attorney, Agent, or Firm* — McGlew and Tuttle, P.C.

(57) ABSTRACT

A method for measuring the anesthetic agent consumption in a ventilation system has a breathing circuit which contains a gas mixer (1) and an anesthetic agent metering device (2). The anesthetic agent quantity, which is consumed over a pregiven time interval in the ventilation system, is determined from the sum of the determined anesthetic gas volume flows in the ventilation system which are integrated over the pregiven time interval.

3 Claims, 1 Drawing Sheet

(56) References Cited

U.S. PATENT DOCUMENTS

| | | | | |
|---|---|---|---|---|
| 5,957,129 | A * | 9/1999 | Tham et al. | 128/204.28 |
| 6,216,690 | B1 * | 4/2001 | Keitel et al. | 128/203.12 |
| 6,325,978 | B1 * | 12/2001 | Labuda et al. | 422/84 |
| 6,679,259 | B2 * | 1/2004 | Heesch | 128/204.26 |
| 7,066,913 | B2 | 6/2006 | Kullik et al. | |
| 2002/0095096 | A1 * | 7/2002 | Mault | 600/531 |
| 2005/0072420 | A1 * | 4/2005 | Gershteyn | A61M 16/104 128/200.19 |
| 2005/0217671 | A1 * | 10/2005 | Fisher et al. | 128/204.18 |
| 2006/0196505 | A1 * | 9/2006 | Izuchukwu | 128/203.15 |
| 2006/0201503 | A1 * | 9/2006 | Breen | 128/204.18 |
| 2006/0254586 | A1 * | 11/2006 | Berry et al. | 128/204.16 |
| 2006/0290525 | A1 * | 12/2006 | Andersen | A61M 16/0051 340/632 |

* cited by examiner

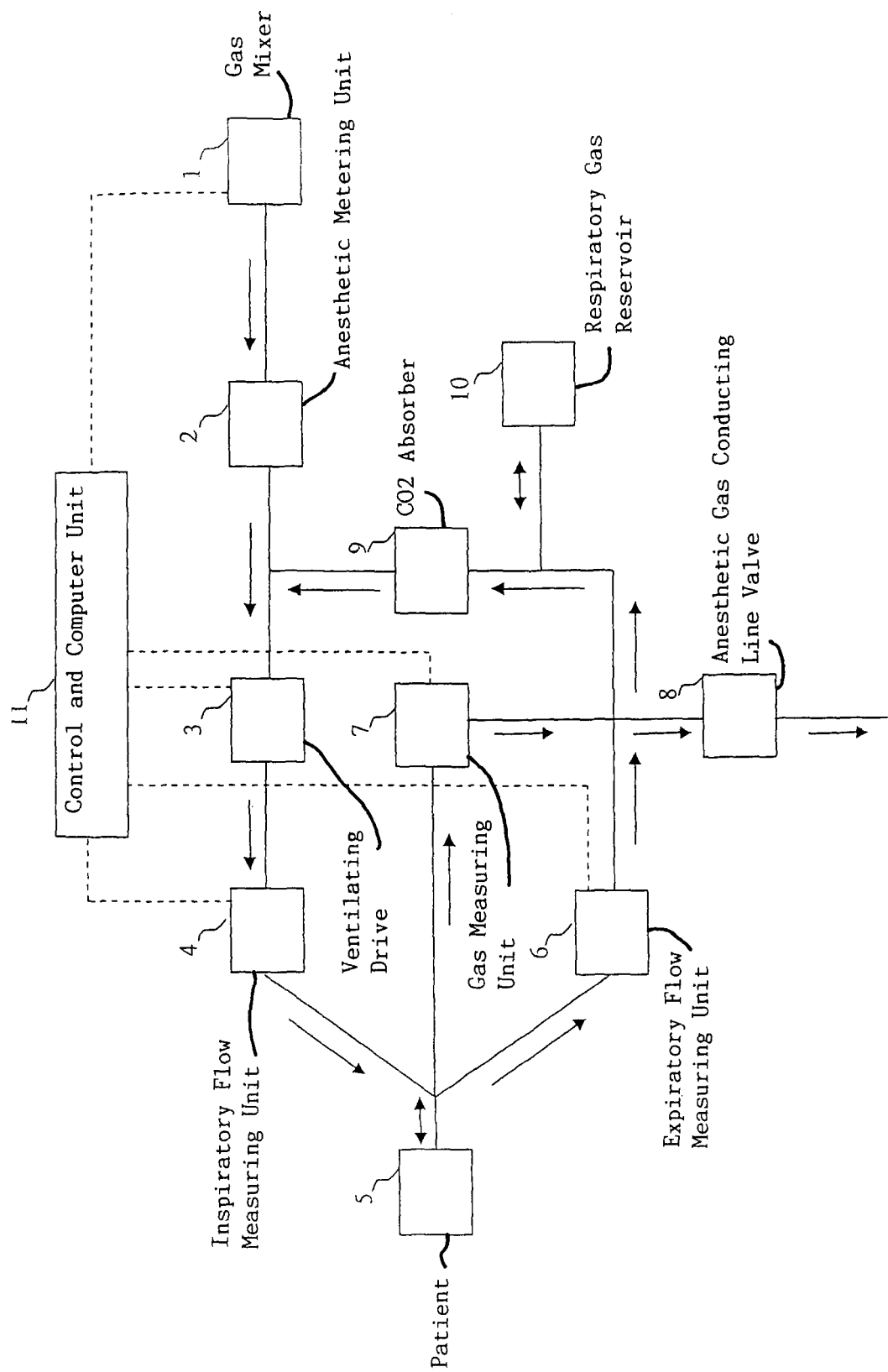

METHOD FOR MEASURING THE ANESTHETIC AGENT CONSUMPTION IN A VENTILATION SYSTEM

CROSS REFERENCE TO RELATED APPLICATION

This application claims priority of German patent application no. 10 2006 027 052.5, filed Jun. 10, 2006, the entire content of which is incorporated herein by reference.

FIELD OF THE INVENTION

The invention relates to a method for measuring the anesthetic agent consumption in a ventilation system.

BACKGROUND OF THE INVENTION

The area of use of the invention is especially in medical technology with the emphasis being in the area of ventilation and of monitoring of medical apparatus and the patients connected thereto who are being ventilated. To an increasing degree, monitoring parameters become also more important which do not themselves function for monitoring the patient or the apparatus status but afford a possibility to detect and to control the consumption of operating agents such as anesthetic gases. This is especially true, inter alia, because of the increasing cost pressures in medicine. A cost factor, which participates essentially with respect to an anesthesia, is the consumption of volatile anesthetic gases, namely, halothane, isoflurane, enflurane, sevoflurane and desflurane.

In most ventilation systems and especially in anesthesia apparatus, these volatile anesthetic agents are not electronically applied and especially vaporized but are rather applied via purely mechanical metering units which do not communicate electronically with the anesthesia apparatus. An example of an anesthetic agent metering device of this kind is available in the marketplace from Drager Medical AG & Co. KG under the product name "Vapor 2000". Therefore, the consumptions of liquid volatile anesthetic agents, which are associated therewith, can not be directly determined and a consumption analysis cannot take place referred to a specific workplace or anesthetist. Especially in a low-flow anesthesia in a breathing circuit, the adjustment of the concentration at the anesthetic agent metering device (Vapor 2000) deviates greatly from the concentration measured at the patient so that no direct conclusion can be drawn from this measured value as to the anesthetic medium flow taken from the anesthetic agent metering device.

A measurement of the consumption of liquid volatile anesthetic agents does not take place with mechanical anesthetic agent vaporizers.

SUMMARY OF THE INVENTION

In view of the above, it is an object of the invention to provide a method for measuring the anesthetic agent consumption in a ventilation system having a breathing circuit and an anesthetic agent metering device contained therein which cannot be read out electrically. An anesthetic agent metering device of this kind is an anesthetic agent vaporizer.

The method of the invention is for measuring consumption of an anesthetic agent in a ventilation system having a breathing circuit containing a gas mixer and an anesthetic agent metering device. The method includes the method steps of: integrating determined anesthetic gas volume flows over a pregiven time interval; and, determining a quantity of the anesthetic agent consumed over the pregiven time interval from the sum of the anesthetic gas volume flows in the ventilation system.

The essential advantage of the above method is the simple determination of the anesthetic agent consumption in a ventilation system from the sum of the anesthetic volume flows in the ventilation system which are determined and integrated over a pregiven time interval.

The subject matter of the invention is therefore a method for measuring the consumption of the anesthetic agent during the anesthesia, especially for a low-flow anesthesia of a patient, without an additional ($2^{nd}$) gas measurement being needed in the anesthesia apparatus.

BRIEF DESCRIPTION OF THE DRAWING

The invention will now be described with reference to the single FIGURE of the drawing (FIG. 1) which shows the configuration of a ventilation system by way of example.

DESCRIPTION OF THE PREFERRED EMBODIMENTS OF THE INVENTION

The ventilation system shown is related to those commercially sold by Drager Medical AG & Co. KG and belonging to the "Drager PRIMUS Family". The arrows in FIG. 1 indicate the direction of the gas flow to and from a component. Valves which ensure the gas flow direction are not shown in FIG. 1 because they are not needed for the principle described herein of the determination of anesthetic agent consumption. Only the direction of the gas flows is decisive. The broken lines without an indicated gas flow direction identify electrical connections and/or data lines on which data are transmitted to a central control and computer unit 11.

In the gas mixer 1, a gas mixture is conducted to the breathing circuit of the ventilation system in accordance with the setting of the user. The gas mixture is usually composed of the individual gases: oxygen (O2), air and nitrous oxide (N2O). This gas flow is usually characterized as a mixture gas. The volume of the mixture gas flow is fed back to the control and computer unit 11. The gas mixer 1 can be a mechanical mixer which is equipped with an electronic gas volume flow measuring device. Or, the gas mixer 1 can also be an electronic mixer which receives the metering data from the control and computer unit 11.

The mixture gas flow is conducted to the anesthetic agent metering device 2 configured here specifically as an anesthetic agent vaporizer. Here, anesthetic vapor is added to the mixture gas flow in correspondence to the adjustment of the user which is not known to the control and computer unit 11 whereby the volume of the gas flow supplied to the ventilation system increases. This gas flow is usually referred to as "fresh gas".

The expiratory respiration gas originates from the patient 5 and is liberated from CO2 in the absorber 9. On the path to the ventilating drive 3, the fresh gas is mixed with the expiratory respiration gas and is volume or pressure controlled in the ventilating drive 3 and conveyed via the inspiratory flow measuring unit 4 to the patient 5. The inspiratory flow measuring unit 4 transmits the measured flow data (that is, the volume flow data) to the control and computer unit 11.

Alternative to an inspiratory flow measuring unit 4, this needed volume data can also be generated from the ventilating drive 3.

The ventilating drive 3 is, for example, a piston unit or compressor unit. After an inspiratory phase, the patient 5 can again deliver his expiratory flow to the ventilation system via the expiratory flow measuring unit 6. The expiratory flow measuring unit 6 supplies the measured volume data to the control and computer unit 11.

The expiratory flow subdivides into different branches. A first part is inputted to the breathing or respiratory gas reservoir 10. In other ventilation systems, this breathing gas reservoir can be identical to the ventilating drive 3 wherefrom at the start of the next inspiratory phase, the breathing gas volume temporarily/intermittently stored in the reservoir 10 can then, flowing through the CO2 absorber 9, be again available to the ventilating drive 3.

A second part of the expiratory breathing gas is supplied to an anesthetic gas conducting line via the anesthetic gas conducting line valve 8. The anesthetic gas conducting line valve 8 opens only starting with a defined system internal pressure so that first the breathing gas reservoir 10 is completely filled before anesthetic gas is lost to the ventilation system.

The so-called Y-piece defines the connecting location of the inspiratory and the expiratory connections of the ventilation system to the patient 5. At this connecting location, the gas concentrations (especially O2, CO2, N2O, volatile anesthetic gases) are measured during the ventilation. This can take place with a so-called suction (sidestream) gas measurement or a gas measurement unit integrated into or connected to the Y-piece and measuring directly. In FIG. 1, this is shown by the suction gas measuring unit 7 which returns the gas flow drawn off by suction again to the ventilation system.

The determination of the anesthetic agent consumption is based upon the premise that all gaseous anesthetic gases, which are consumed within the system, must have been supplied from the mechanical anesthetic agent vaporizer. The balance of the gases taken to those delivered must therefore be maintained. All anesthetic gas losses are summed up and their pure anesthetic gas flows are integrated over a time period.

The time period of the integration can, for example, be set from the start of a surgical procedure up to the end of the particular surgical procedure. In this way, one obtains, for example, the anesthetic gas quantity consumed for the particular surgical procedure.

The anesthetic gas reductions or losses in the system shown in FIG. 1 are as follows:

(a) the patient 5 who, at the start of the surgical procedure, has a larger anesthetic gas uptake and then a slowly reducing anesthetic gas uptake. This anesthetic gas quantity, which is consumed in this manner, is determined from the difference of the inspiratory anesthetic gas concentration to the expiratory anesthetic gas concentrations, multiplied by the breathing minute volume flow of the patient 5.

(b) a possibly present leakage in the patient loop (the region of the patient connectors such as a Y-piece, tubes and their connections, intubation tube and its connectors, possibly a larynx mask, et cetera) which is illustrated in FIG. 1 by the region coming from the flow measuring unit 4, going to the patient 5 and returning to the flow measuring unit 6. The anesthetic gas quantity, which is consumed in this manner, is determined from the measured leakage volume flow, that is, from the difference of the inspiratory applied volume flow and the expiratory volume flow exhaled by the patient 5 and corrected by the total gas uptake of the patient multiplied by an anesthetic gas concentration which lies between the inspiratory and expiratory measured anesthetic gas concentrations. In the simplest embodiment, the anesthetic gas concentration used therefore is a mean value of the inspiratory and the expiratory anesthetic gas concentrations but can also be determined more precisely in accordance with the given pressure and time conditions of the inspiration and the expiration.

(c) the total volume flow, which flows via the anesthetic gas conducting line valve 8 into the anesthetic gas conducting line, multiplied by the expiratory measured anesthetic gas concentration. The volume of the volume flow to the anesthetic gas conducting line is computed from the volume flow of the fresh gas, which is supplied in total to the system, reduced by the total gas uptake of the patient, the leakage of the total system and the CO2 volume flow absorbed in the CO2 absorber 9. The CO2 volume is the expiratory CO2 concentration multiplied by the expiratory exhaled volume flow of the patient 5.

(d) if the drawn off volume flow of the gas measuring unit 7 is not returned to the ventilation system but is likewise conducted into the anesthetic gas conducting line then this volume flow, too, multiplied by the correspondingly measured anesthetic gas concentration, is also to be considered.

(e) the anesthetic gas volume flow needed for an increase of the anesthetic gas concentration in the ventilation system itself also defines a relevant component. At the start of a surgical procedure, as a rule, anesthetic agent free ventilating gas is applied and only during the course of the ventilation, anesthetic gas is flooded in. A portion of the anesthetic gas volume flow, which is taken from the anesthetic agent vaporizer, is needed so that the breathing system volume is raised to a higher anesthetic agent concentration. This can be determined from the breathing system volume multiplied by the increase of the anesthetic gas concentration since the start of the particular surgical procedure.

This assessment applies especially for the region wherein the breathing minute volume flow is less than the fresh gas volume flow supplied to the ventilation system. If the fresh gas volume flow is greater than the breathing minute volume flow, then the assessment of the gas volume flows will determine too low a value because the volume flow into the anesthetic gas conducting line is multiplied by the expiratory anesthetic gas concentrations, but fresh gas concentration values, which are significantly higher, are also discharged into the anesthetic gas conducting line.

The method of the invention provides an assessment of the resulting overall consumption of anesthetics by and in the ventilation system by summing up all the individual anesthesia gas volume flows of the ventilation system within a certain time interval.

For a supply of a fresh gas volume flow so high, the inspiratory measured anesthetic gas concentration is, however, equal to the concentration adjusted at the anesthetic agent vaporizer so that the consumption can be determined directly from the fresh gas volume flow multiplied by the inspiratory measured anesthetic gas concentration.

This value is, however, too low when the fresh gas volume flow is less than the breathing minute volume flow of the patient 5. In the simplest case, and in order to not have to perform a complex computation of the transition point/switchover point, the gaseous anesthetic agent consumption can be determined from the larger of the two values generated from the gas assessment and the fresh gas referenced determination of the anesthetic agent consumption.

This can take place separately for each applied anesthetic gas with this application being the simultaneous application of more than one anesthetic gas or the application of more than one anesthetic gas in time sequence. The total gaseous consumptions of anesthetic gases, which are so determined in this manner, are then converted into the liquid consumption of the particular anesthetic agent, especially in the control and computer unit 11. The total gaseous consumptions so determined are converted while considering the ambient temperature, the ambient pressure and the vaporization factor specific to the particular anesthetic gas. Both the ambient temperature and the ambient pressure can be already measured in the system or can also be manually adjusted. This method can likewise be applied for the anesthetic gas uptake of the patient 5 so that a relation is obtained of consumed anesthetic agent to the minimally needed anesthetic agent.

The anesthetic agent consumptions so determined can then be displayed as well as transmitted further to a central location via a possibly already available data communication.

From the totality of the data of different surgical procedures, the consumption and cost computations can be generated and requirements as to anesthetic agents can be planned in time or even training requirements can be determined when, for specific anesthetists, the anesthetic agent consumption is relatively high compared to the surgery time or to the anesthetic gas uptake of the patient.

Furthermore, these values can also be used in the anesthesia apparatus itself in order to provide an aid to the anesthetist during the anesthesia as he/she can avoid an unnecessarily high consumption of anesthetic agent (for example, low-flow trainer, economy meter).

It is understood that the foregoing description is that of the preferred embodiments of the invention and that various changes and modifications may be made thereto without departing from the spirit and scope of the invention as defined in the appended claims.

What is claimed is:

1. A method for measuring consumption of an anesthetic agent over a time interval, the method comprising the steps of:
   providing a ventilation system comprising a breathing circuit, an inspiratory line, an expiratory line and a Y-piece connecting the inspiratory line and the expiratory line to a patient, a gas mixer providing fresh gas to the breathing circuit, a manually actuatable anesthetic agent metering device for metering anesthetic to the fresh gas that is added to the breathing circuit, a gas measuring unit measuring anesthetic gas concentration at the Y-piece, an inspiratory volume flow measuring unit, at least a further volume flow measuring unit and a ventilating drive connected to the breathing circuit;
   providing a control and computer unit operatively connected to each of the gas measuring unit, the inspiratory volume flow measuring unit, the further volume flow measuring unit and the ventilating drive and not electrically and not operatively connected to the manually actuatable anesthetic agent metering device;
   manually setting and manually adjusting the setting of the manually actuatable anesthetic agent metering device to set and manually adjust an anesthetic concentration of anesthetic metered to the fresh gas and feeding the fresh gas with the set and adjusted anesthetic concentration to the breathing circuit during the course of a ventilation system procedure, wherein the manually actuatable anesthetic agent metering device does not communicate electronically with the ventilation system during the course of the ventilation system procedure;
   determining an inspiratory anesthetic gas concentration of the anesthetic agent and an expiratory anesthetic gas concentration of the anesthetic agent with the gas measuring unit;
   calculating a patient uptake anesthetic gas volume flow by multiplying a difference of the inspiratory anesthetic gas concentration and the expiratory anesthetic gas concentration with a measured inspiratory breathing minute volume flow;
   determining an anesthetic gas removal volume flow via an anesthetic gas removal conducting line;
   determining at least one further anesthetic gas volume flow of the ventilation system, the determination comprising determining any combination of:
   an anesthetic gas leakage volume flow from a patient loop;
   an anesthetic gas quantity drawn off volume flow of the gas measuring unit that is not returned to the ventilation system; and
   an anesthetic gas concentration increase volume flow for an increase of anesthetic gas concentration in the ventilation system;
   integrating a patient uptake anesthetic gas volume flow and the at least one further anesthetic gas volume flow over the time interval corresponding to a duration of a ventilation system procedure to provide a value of a volume of anesthetic gas consumed by the ventilation system during the ventilation system procedure; and
   recording the value, wherein:
   the at least a further volume flow measuring unit comprises or is associated with the gas mixer;
   a $CO_2$ absorber is connected to the breathing circuit;
   the anesthetic gas removal volume flow is a removal volume flow via an anesthetic gas removal conducting line multiplied by the expiratory anesthetic gas concentration wherein the removal volume flow is determined from a total fresh gas volume flow supplied as determined by the gas mixer to the ventilation system reduced by a total gas uptake of the patient, reduced by a gas quantity consumed by a leakage volume flow by the ventilation system and reduced by a $CO_2$ volume absorbed in the $CO_2$ absorber wherein the $CO_2$ volume is an expiratory $CO_2$ concentration multiplied by an expiratory exhaled volume flow of the patient.

2. A method for measuring consumption of an anesthetic agent, the method comprising the steps of:
   providing a ventilation system comprising a breathing circuit, an inspiratory line, an expiratory line, a Y-piece connecting the inspiratory line and the expiratory line to a patient, a gas mixer providing fresh gas to the breathing circuit, a manually actuatable anesthetic agent metering device for metering anesthetic to the fresh gas that is added to the breathing circuit, an anesthetic gas removal conducting line connected to the breathing circuit, a $CO_2$ absorber connected to the breathing circuit, a gas measuring unit measuring anesthetic gas, $O_2$, $CO_2$, and $N_2O$ concentration at the Y-piece, an inspiratory flow measuring unit, at least a further volume flow measuring unit and a ventilating drive connected to the breathing circuit;
   providing a control and computer unit operatively connected to each of the gas measuring unit, the inspiratory volume flow measuring unit, the further volume flow measuring unit and the ventilating drive and not electrically and not operatively connected to the manually actuatable anesthetic agent metering device;

manually setting and manually adjusting the setting of the manually actuatable anesthetic agent metering device to set and manually adjust an anesthetic concentration of anesthetic metered to the fresh gas and feeding the fresh gas with the set and adjusted anesthetic concentration to the breathing circuit during the course of a ventilation system procedure, wherein the manually actuatable anesthetic agent metering device does not communicate electronically with the ventilation system during the course of the ventilation system procedure;

determining an inspiratory anesthetic gas concentration of the anesthetic agent and an expiratory anesthetic gas concentration of the anesthetic agent with the gas measuring unit;

determining a plurality of anesthetic gas volume flows associated with consumption of the anesthetic agent by elements of the ventilation system, wherein the patient is one of the elements of the ventilation system and an anesthetic gas removal volume flow via an anesthetic gas removal conducting line is another of the elements of the ventilation system, and determining a plurality of anesthetic gas volume flows associated with consumption of the anesthetic agent by elements of the ventilation system comprises:

determining a patient uptake anesthetic gas volume flow by multiplying a difference of the inspiratory anesthetic gas concentration and the expiratory anesthetic gas concentration with an inspiratory breathing minute volume flow; and determining a gas removal conducting line anesthetic gas volume flow by measuring flow from a total fresh gas volume flow supplied to the breathing circuit as determined by the gas mixer to the ventilation system reduced by a total gas uptake of the patient, reduced by a gas quantity consumed by a leakage volume flow by the ventilation system and reduced by a $CO_2$ volume absorbed in the $CO_2$ absorber, wherein the $CO_2$ volume is an expiratory $CO_2$ concentration, multiplied by an expiratory exhaled volume flow of the patient, to provide a total gas removal conducting line volume flow and multiplying the total gas removal conducting line volume flow by the expiratory anesthetic gas concentration;

integrating the patient uptake anesthetic gas volume flow and the gas removal conducting line anesthetic gas volume flow over a time interval corresponding to the duration of the ventilation system procedure to provide an anesthetic gas consumption value during the ventilation system procedure; and recording the anesthetic gas consumption value.

3. The method according to claim 2, wherein:

a patient loop is another of the elements of the ventilation system;

determining a plurality of anesthetic gas volume flows associated with consumption the anesthetic agent further comprises determining an anesthetic gas leakage volume flow from the patient loop based on a difference of an inspiratory applied volume flow and an expiratory volume flow exhaled by the patient corrected by a total gas uptake of the patient multiplied by an anesthetic gas concentration at a location between the inspiratory and expiratory measured anesthetic gas concentrations or multiplied by a mean value of the inspiratory anesthetic gas concentration and the expiratory anesthetic gas concentration; and the step of integrating further comprises integrating the anesthetic gas leakage volume flow over the time interval to provide the anesthetic gas consumption value during the ventilation system procedure.

* * * * *